(12) United States Patent
Eidenschink

(10) Patent No.: US 7,367,989 B2
(45) Date of Patent: *May 6, 2008

(54) ROTATING BALLOON EXPANDABLE SHEATH BIFURCATION DELIVERY

(75) Inventor: Tracee Eidenschink, Wayzata, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 510 days.

This patent is subject to a terminal disclaimer.

(21) Appl. No.: 10/375,689

(22) Filed: Feb. 27, 2003

(65) Prior Publication Data

US 2004/0172119 A1   Sep. 2, 2004

(51) Int. Cl.
*A61F 2/06* (2006.01)

(52) U.S. Cl. ..................... 623/1.11; 606/194

(58) Field of Classification Search ............. 606/108, 606/191–198; 604/96.01, 101.01, 103.03, 604/103.04, 103.05, 264; 623/1.11, 1.12
See application file for complete search history.

(56) References Cited

U.S. PATENT DOCUMENTS

| | | | |
|---|---|---|---|
| 4,448,195 A | 5/1984 | Leveen et al. | 128/344 |
| 4,484,585 A | 11/1984 | Baier | 128/748 |
| 4,601,701 A | 7/1986 | Mueller, Jr. | 604/83 |
| 4,769,005 A | 9/1988 | Ginsburg et al. | 604/53 |
| 4,776,337 A | 10/1988 | Palmaz | 128/343 |
| 4,913,141 A | 4/1990 | Hillstead | 606/108 |
| 4,994,071 A | 2/1991 | MacGregor | 606/194 |
| 4,998,923 A | 3/1991 | Samson et al. | 606/194 |
| 5,019,085 A | 5/1991 | Hillstead | 606/108 |
| 5,120,308 A | 6/1992 | Hess | |
| 5,122,154 A | 6/1992 | Rhodes | 606/198 |
| 5,195,984 A | 3/1993 | Schatz | 606/195 |
| 5,219,355 A | 6/1993 | Parodi et al. | 606/191 |
| 5,316,023 A | 5/1994 | Palmaz et al. | 128/898 |
| 5,380,299 A | 1/1995 | Fearnot et al. | |
| 5,397,305 A | 3/1995 | Kawula et al. | 604/96 |
| 5,449,353 A | 9/1995 | Samson et al. | |
| 5,449,382 A | 9/1995 | Dayton | |
| 5,477,856 A | 12/1995 | Lundquist | |
| 5,556,413 A * | 9/1996 | Lam | 623/1.2 |
| 5,571,086 A | 11/1996 | Kaplan et al. | |
| 5,609,627 A | 3/1997 | Goicoechea et al. | 623/1 |
| 5,632,763 A | 5/1997 | Glastra | 606/194 |
| 5,643,278 A | 7/1997 | Wijay | 606/108 |
| 5,683,345 A | 11/1997 | Waksman et al. | |

(Continued)

FOREIGN PATENT DOCUMENTS

DE   297 01 758   5/1997

(Continued)

OTHER PUBLICATIONS

Foley et al., "Bifurcation Lesion Stenting", *The Thoraxcentre Journal*, vol. 8, No. 4, (1996).

(Continued)

*Primary Examiner*—Michael J. Hayes
*Assistant Examiner*—Victor Nguyen
(74) *Attorney, Agent, or Firm*—Merchant & Gould P.C.

(57) ABSTRACT

A medical device comprises a balloon catheter shaft having a catheter balloon. An outer balloon or sheath is disposed about the catheter balloon and is freely rotatable about the catheter balloon.

31 Claims, 7 Drawing Sheets

U.S. PATENT DOCUMENTS

| | | |
|---|---|---|
| 5,697,971 A | 12/1997 | Fischell et al. |
| 5,725,519 A | 3/1998 | Penner et al. .................. 606/1 |
| 5,749,825 A | 5/1998 | Fischell et al. ................ 600/3 |
| 5,755,734 A | 5/1998 | Richter et al. ............. 606/194 |
| 5,755,735 A | 5/1998 | Richter et al. ............. 606/194 |
| 5,755,778 A | 5/1998 | Kleshinski ..................... 623/1 |
| 5,772,669 A | 6/1998 | Vrba |
| 5,776,141 A | 7/1998 | Klein et al. |
| 5,797,952 A | 8/1998 | Klein ......................... 606/198 |
| 5,817,100 A * | 10/1998 | Igaki ........................ 623/1.11 |
| 5,824,055 A | 10/1998 | Spiridigliozzi et al. ........ 623/1 |
| 5,836,952 A * | 11/1998 | Davis et al. ................ 606/108 |
| 5,843,027 A | 12/1998 | Stone et al. |
| 5,873,906 A | 2/1999 | Lau et al. ....................... 623/1 |
| 5,876,374 A | 3/1999 | Alba et al. |
| 5,893,868 A | 4/1999 | Hanson et al. |
| 5,906,640 A | 5/1999 | Penn et al. |
| 5,908,405 A | 6/1999 | Imran et al. |
| 5,921,995 A | 7/1999 | Kleshinski |
| 5,935,161 A | 8/1999 | Robinson et al. |
| 5,941,908 A | 8/1999 | Glodsteen et al. ............. 623/1 |
| 5,951,569 A | 9/1999 | Tuckey et al. |
| 5,957,929 A | 9/1999 | Brenneman |
| 5,961,546 A | 10/1999 | Robinson et al. |
| 5,961,548 A | 10/1999 | Shmulewitz |
| 6,013,092 A | 1/2000 | Dehdashtian et al. ....... 606/194 |
| 6,015,424 A | 1/2000 | Rosenbluth et al. |
| 6,017,362 A | 1/2000 | Lau ............................... 623/1 |
| 6,027,460 A | 2/2000 | Shturman ................... 600/585 |
| 6,033,434 A | 3/2000 | Borghi ........................... 623/1 |
| 6,048,350 A * | 4/2000 | Vrba ........................ 623/1.11 |
| 6,048,361 A | 4/2000 | Von Oepen .................... 623/1 |
| 6,056,722 A | 5/2000 | Jayaraman .................. 604/102 |
| 6,056,775 A | 5/2000 | Borghi et al. .............. 623/1.16 |
| 6,059,813 A | 5/2000 | Vrba et al. ................. 606/198 |
| 6,071,286 A | 6/2000 | Mawad ....................... 606/108 |
| 6,077,297 A | 6/2000 | Robinson et al. .......... 623/1.11 |
| 6,090,127 A | 7/2000 | Globerman ................. 606/194 |
| 6,096,073 A | 8/2000 | Webster et al. ............ 623/1.16 |
| 6,099,497 A * | 8/2000 | Adams et al. .......... 604/96.01 |
| 6,110,191 A | 8/2000 | Dehdashtian et al. ....... 606/192 |
| 6,117,156 A | 9/2000 | Richter et al. ............. 606/194 |
| 6,120,522 A | 9/2000 | Vrba et al. ................. 606/190 |
| 6,132,450 A | 10/2000 | Hanson et al. ............. 606/198 |
| 6,143,014 A | 11/2000 | Dehdashtian et al. ....... 606/192 |
| 6,146,415 A | 11/2000 | Fitz ............................ 623/1.11 |
| 6,152,944 A | 11/2000 | Holman et al. ............ 623/1.11 |
| 6,165,195 A | 12/2000 | Wilson et al. .............. 606/194 |
| 6,165,210 A | 12/2000 | Lau et al. ................... 623/1.12 |
| 6,187,015 B1 | 2/2001 | Brenneman ................. 606/108 |
| 6,190,360 B1 | 2/2001 | Iancea et al. .......... 604/164.09 |
| 6,190,393 B1 | 2/2001 | Bevier et al. ............... 606/108 |
| 6,210,380 B1 | 4/2001 | Mauch ........................ 604/284 |
| 6,210,431 B1 | 4/2001 | Power ........................ 623/1.11 |
| 6,221,090 B1 | 4/2001 | Wilson ....................... 606/194 |
| 6,221,097 B1 | 4/2001 | Wang et al. ................ 623/1.11 |
| 6,224,587 B1 | 5/2001 | Gibson ........................ 604/528 |
| 6,238,410 B1 | 5/2001 | Vrba et al. ................. 606/198 |
| 6,246,914 B1 | 6/2001 | De la Rama et al. ........ 607/122 |
| 6,254,593 B1 | 7/2001 | Wilson ....................... 606/1.11 |
| 6,258,052 B1 | 7/2001 | Milo ............................. 604/22 |
| 6,258,073 B1 | 7/2001 | Mauch ........................ 604/284 |
| 6,264,688 B1 | 7/2001 | Herklotz et al. ............ 623/1.16 |
| 6,280,466 B1 | 8/2001 | Kugler et al. .............. 623/1.12 |
| 6,287,277 B1 | 9/2001 | Yan .......................... 604/96.01 |
| 6,287,330 B1 | 9/2001 | Johansson et al. ......... 623/1.13 |
| 6,290,673 B1 | 9/2001 | Shanley ................. 604/102.02 |
| 6,299,636 B1 | 10/2001 | Schmitt et al. .............. 623/1.2 |
| 6,302,906 B1 | 10/2001 | Goicoechea et al. ....... 623/1.11 |
| 6,319,275 B1 | 11/2001 | Lashinski et al. .......... 623/1.11 |
| 6,322,548 B1 | 11/2001 | Payne et al. ................. 604/500 |
| 6,361,544 B1 | 3/2002 | Wilson et al. ............... 606/194 |
| 6,361,555 B1 | 3/2002 | Wilson ....................... 623/1.11 |
| 6,364,893 B1 | 4/2002 | Sahatjian et al. ........... 606/194 |
| 6,371,978 B1 | 4/2002 | Wilson ....................... 623/1.11 |
| 6,375,660 B1 | 4/2002 | Fischell et al. .............. 606/108 |
| 6,379,372 B1 | 4/2002 | Dehdashtian et al. ....... 606/192 |
| 6,387,120 B2 | 5/2002 | Wilson et al. .............. 623/1.11 |
| 6,391,050 B1 | 5/2002 | Broome ..................... 623/1.11 |
| 6,406,487 B2 | 6/2002 | Brenneman ................ 623/1.11 |
| 6,406,489 B1 | 6/2002 | Richter et al. ............. 623/1.16 |
| 6,416,529 B1 | 7/2002 | Holman et al. ............. 606/194 |
| 6,436,104 B2 | 8/2002 | Hojeibane ................... 606/108 |
| 6,443,980 B1 | 9/2002 | Wang et al. ................ 623/1.35 |
| 6,471,672 B1 * | 10/2002 | Brown et al. .......... 604/101.01 |
| 6,475,166 B1 | 11/2002 | Escano ........................ 600/585 |
| 6,482,211 B1 | 11/2002 | Choi ........................... 606/108 |
| 6,488,694 B1 | 12/2002 | Lau et al. .................... 606/194 |
| 6,508,835 B1 | 1/2003 | Shaolian et al. ........... 623/1.35 |
| 6,514,281 B1 | 2/2003 | Blaeser et al. ............. 623/1.12 |
| 6,520,983 B1 | 2/2003 | Colgan et al. ............. 623/1.11 |
| 6,520,988 B1 | 2/2003 | Colombo et al. .......... 623/1.35 |
| 6,530,947 B1 | 3/2003 | Euteneuer et al. ......... 623/1.11 |
| 6,533,805 B1 | 3/2003 | Jervis ......................... 623/1.11 |
| 6,540,719 B2 | 4/2003 | Bigus et al. ............ 604/96.01 |
| 6,554,841 B1 | 4/2003 | Yang ........................... 606/108 |
| 6,569,180 B1 | 5/2003 | Sirhan et al. |
| 6,582,459 B1 | 6/2003 | Lau et al. ................... 623/1.11 |
| 6,589,262 B1 | 7/2003 | Honebrink et al. ......... 606/191 |
| 6,596,020 B2 | 7/2003 | Vardi et al. ................. 623/1.11 |
| 6,599,315 B2 | 7/2003 | Wilson ....................... 623/1.11 |
| 6,602,226 B1 | 8/2003 | Smith et al. ........... 604/103.05 |
| 6,607,506 B2 | 8/2003 | Kletschka ................ 604/96.01 |
| 6,613,067 B1 | 9/2003 | Johnson ...................... 606/194 |
| 6,629,981 B2 | 10/2003 | Bui et al. .................... 606/108 |
| 6,660,030 B2 | 12/2003 | Shaolian et al. |
| 6,669,718 B2 | 12/2003 | Basselink ................... 623/1.11 |
| 6,692,483 B2 | 2/2004 | Vardi et al. |
| 2001/0049548 A1 | 12/2001 | Vardi et al. ................. 623/1.11 |
| 2002/0019664 A1 | 2/2002 | Douglas ..................... 623/1.35 |
| 2002/0019665 A1 | 2/2002 | Dehdashtian et al. ...... 623/1.35 |
| 2002/0022874 A1 | 2/2002 | Wilson ....................... 623/1.11 |
| 2002/0038140 A1 | 3/2002 | Yang et al. ................. 623/1.12 |
| 2002/0038141 A1 | 3/2002 | Yang et al. ................. 623/1.12 |
| 2002/0072755 A1 | 6/2002 | Bigus et al. ................ 606/108 |
| 2002/0111675 A1 | 8/2002 | Wilson ....................... 623/1.35 |
| 2002/0116045 A1 | 8/2002 | Eidenschink ............... 623/1.11 |
| 2002/0120320 A1 | 8/2002 | Wang et al. ................ 623/1.11 |
| 2002/0165598 A1 | 11/2002 | Wahr et al. |
| 2003/0023298 A1 | 1/2003 | Jervis |
| 2003/0055483 A1 | 3/2003 | Gumm ........................ 623/1.11 |
| 2003/0055484 A1 | 3/2003 | Lau et al. ................... 623/1.13 |
| 2003/0130716 A1 | 7/2003 | Weber et al. ............... 623/1.11 |
| 2003/0181923 A1 | 9/2003 | Vardi |
| 2003/0195546 A1 | 10/2003 | Solar et al. ................. 606/192 |

FOREIGN PATENT DOCUMENTS

| | | |
|---|---|---|
| FR | 2 678 508 A1 | 1/1993 |
| WO | 03/017872 A1 | 3/2003 |
| WO | 03/055414 | 7/2003 |
| WO | WO 03/061529 A1 | 7/2003 |

OTHER PUBLICATIONS

Schampaert, MD, Erick et al., "The V-Stent: A Novel Technique for Coronary Bifurcation Stenting", *Catheterization and Cardiovascular Diagnosis*, 39:320-326 (1996).

Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).

U.S. Appl. No. 10/375,689, filed Feb. 27, 2003, Eidenschink.

U.S. Appl. No. 10/747,546, filed Dec. 29, 2003, Eidenschink et al.

Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).

Oda, MD., et al., "Fork Stenting for Bifurcational Lesion", Journal of Interventional Cardiology, vol. 9, No. 6, pp. 445-454 (Dec. 1996).

Nakamura et al., "Techniques for Palmaz-Schatz Stent Deployment in Lesions With a Large Side Branch", Catheterization and Cardiovascular Diagnosis, vol. 34, pp. 353-361 (1995).

U.S. Appl. No. 10/657,472, filed Sep. 8, 2003, Eidenschink, et al.
U.S. Appl. No. 10/757,646, filed Jan. 13, 2004, Eidenschink, et al.
U.S. Appl. No. 10/780,937, filed Feb. 18, 2004, Eidenschink, et al.
U.S. Appl. No. 10/784,337, filed Feb. 23, 2004, Eidenschink, et al.
U.S. Appl. No. 10/863,724, filed Jun. 8, 2004, Eidenschink, et al.

* cited by examiner

ROTATING BALLOON EXPANDABLE SHEATH BIFURCATION DELIVERY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

Stent systems are widely used in the treatment of stenoses. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

Treatment at bifurcation sites has been difficult. Although efforts have been made to use a stent at bifurcations, these sites have previously been problematic to treat. The specialty stents designed for bifurcations generally need specific alignment, radially as well as longitudinally. For example, U.S. Pat. No. 5,749,825 is representative of a catheter system that treats stenoses at an arterial bifurcation. The disclosure of U.S. Pat. No. 5,749,825 is hereby incorporated by reference.

A stent having different diameters has been proposed to allow placement in both a primary passage, such as an artery, and a secondary passage, such as a side branch artery. Additionally, these stents generally have a circular opening which allows for unimpeded blood flow into the side branch artery. However, problems are still encountered in orienting the stent relative to the side branch at the bifurcation of the primary and secondary passages.

Many current devices rely on either passive torque (e.g., pushing the stent forward and allowing the stent that is fixed on the guide wire/balloon to passively rotate itself into place) or creating torque from outside of the patient to properly orient the medical device in the passage. These devices and methods of achieving proper angular orientation have not been shown to be effective in properly placing and positioning the stent. As will be appreciated and understood by those skilled in the art, improper placement of the stent with respect to its rotational or circumferential orientation, or its longitudinal placement, could lead to obstruction of the side branch passage. It is important to properly position or center an opening formed in the bifurcated stent with the secondary passage to maximize flow therethrough.

Thus, a need exists for effectively treating stenosed passage bifurcations. This need includes more precise and exact longitudinal placement and rotational/circumferential orientation of the stent.

Many commercially available devices do not maintain side branch access at the time of stent deployment. This results in the potential for plaque shift and occlusion of the secondary passage.

It would also be advantageous if stents could be placed across the side branch while wire position is maintained thereby helping to protect and secure further access to the side branch.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the present invention include a freely rotating deployment assembly for a stent assembly maintaining side branch access and protection.

The present invention contemplates an apparatus and method that improves the orientation of a stent by providing a more exact placement of the stent relative to the side branch passage. This, in turn, may lead to better protection of the side branch passage.

At least one embodiment of the invention includes a medical device with a balloon catheter shaft and a rotating sheath. In some embodiments the catheter shaft has a first guide wire lumen therethrough and an inflation lumen extending from a proximal, region of the catheter shaft to a distal region of the catheter shaft.

In at least one embodiment at least a portion of the distal region of the catheter shaft has a balloon disposed about it.

In some embodiments no portion of the sheath is more than about 5 centimeters proximal to the most proximal portion of the balloon.

In at least some embodiments a stent may be situated about the sheath.

In at least one embodiment a second guide wire lumen with a portion disposed under the stent contains a portion of a second guide wire.

In some embodiments the stent is self expanding. In some embodiments the stent is balloon expandable. In some embodiments the stent is made of shape memory material.

In some embodiments the sheath is constructed such that it is radially expandable.

In some embodiments the sheath is constructed such that the stent may be crimped onto the sheath.

In some embodiments the sheath is constructed of at least one homogeneous layer.

In some other embodiments the sheath has a low friction inner surface. In other embodiments a friction reducing substance is placed between the sheath and the inner balloon. In other embodiments a friction reducing substance is placed between an outer balloon and the inner balloon.

In some embodiments the sheath is constructed of a soft durometer polymer.

In at least one embodiment the sheath is constructed of multiple layers.

In at least one embodiment at least one of the layers is constructed of a first material having different properties from a second material found in at least one other layer.

In some other embodiments an inner layer constructed of a low friction material is in contact with the balloon. Materials such as PTFE and HDPE are used in some embodiments.

In some embodiments an outer layer of a soft durometer polymer suitable for securing the stent to the sheath is used.

In some other embodiments the sheath is made of a shape memory material so it shrinks back down for withdrawal.

In some other embodiments the sheath rotates freely.

In at least one other embodiment the longitudinal movement of the sheath relative to the balloon catheter shaft is limited with a safety tether. The safety tether can be a pull wire outside either guidewire lumen or it can be inside the second wire lumen.

In some embodiments the catheter balloon has at least one balloon cone distally offset from the distal most portion of the sheath or proximally offset from the proximal most portion of the sheath.

In some embodiments the assembly has marker bands located about the balloon catheter shaft. In some embodiments the marker bands have a greater diameter than the cross-sectional diameter of the sheath thereby limiting longitudinal movement of the sheath relative to the balloon catheter shaft. In some embodiments at least one marker band has a radiopaque portion.

In some embodiments a rotating collar is positioned about the second wire lumen and the balloon catheter shaft. In other such embodiments a first longitudinal lock is positioned about the second wire lumen and proximal to the rotating collar, and a second longitudinal lock is positioned about the balloon catheter shaft and distal to the rotating collar such that the longitudinal position of the sheath and collar is maintained.

In some embodiments the medical device has a hypotube engaged to the sheath at the distal end of the hypotube and engaged to the collar at the proximal end of the hypotube.

In some embodiments the hypotube is spiral cut. In some embodiments the hypotube comprises stainless steel. In some embodiments the hypotube comprises a polymer.

In some embodiments the proximal end of the hypotube is disposed in a second guide wire lumen of the collar.

In some embodiments the proximal end of the hypotube is engaged to an outside surface of the collar.

In some embodiments the sheath has a length that is substantially the same as the length of the catheter balloon.

In some embodiments the balloon has a body portion with a cone portion distal to the body portion and a cone portion proximal to the body portion, and the sheath is disposed about the body portion and has a length substantially the same as the length of the body portion of the catheter balloon.

In some embodiments the length of the sheath is no greater than 2 centimeters longer than the length of the balloon.

In some embodiments the sheath extends distally from a location proximal to the proximal end of the catheter balloon. In some embodiments the sheath extends distally from a location equal to or less than 2 centimeters proximal to the proximal end of the catheter balloon.

In some embodiments the assembly provides for proper orientation relative to the side branch, side branch protection with the guide wire during stent deployment, proper placement of the stent both longitudinally and circumferentially, and reduction in the incidence of tangled wires.

In other embodiments an outer balloon may replace the sheath of the above embodiments. The outer balloon in such instances may have the same qualities as the sheath as described in the embodiments above.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
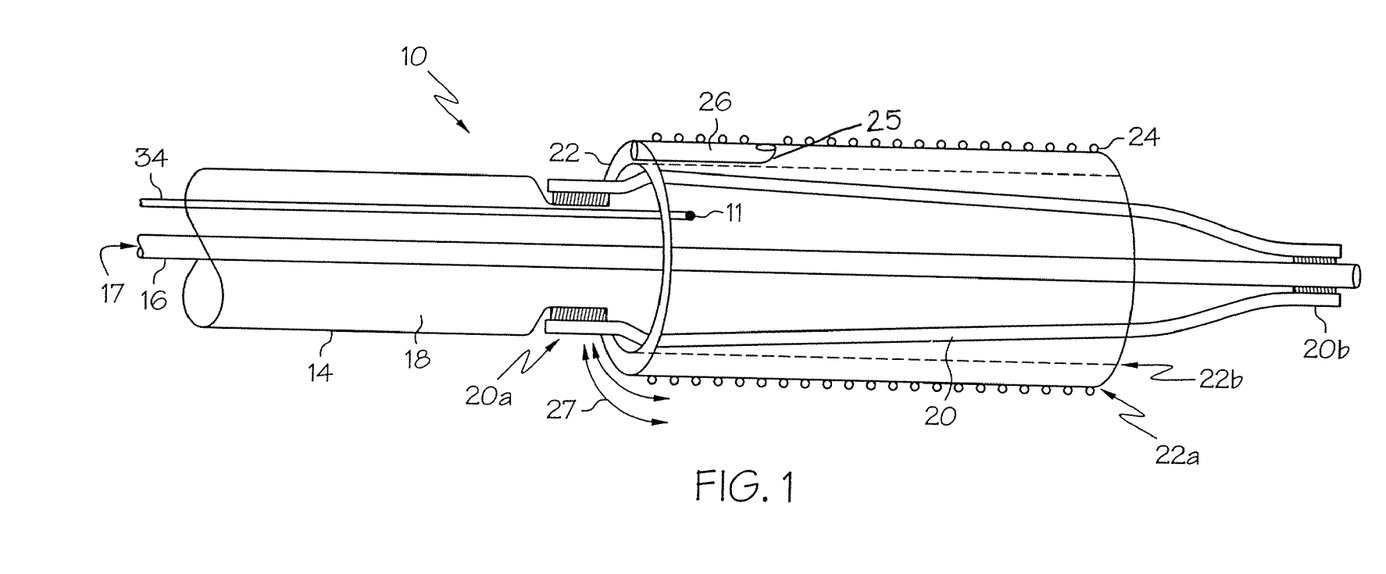
FIG. 1 is a perspective view of an embodiment of the invention wherein the assembly is shown in a pre-deployment configuration.

Referring now to the drawings which are for the purposes of illustrating embodiments of the invention only and not for purposes of limiting same, in at least one embodiment of the invention, an example of which is shown in FIG. 1, an assembly 10 is shown. The assembly is designed to provide better axial and longitudinal positioning of a stent in a bifurcation site. The assembly 10 has an outer catheter shaft 14 with an inner catheter shaft 16 defining a wire lumen 17 and an inflation lumen 18 extending from a proximal region of the catheter to a distal region of the catheter. The inner lumen 17 is constructed such that it can be disposed about a guide wire which provides means for guiding the catheter to the treatment site. The inflation lumen 18 provides a passage for the inflating fluid to both inflate and deflate the catheter balloon 20. The catheter balloon 20 is sealingly engaged at its proximal end 20a to the outer shaft 14 and is sealingly engaged at its distal end 20b to the inner shaft 16.

A sheath 22 is disposed about the balloon 20. The sheath is designed to be freely rotatable about the balloon. The sheath 22 can be constructed of a low friction material such as PTFE or HDPE which allows the sheath to freely rotate about the balloon 20. In some embodiments at least a portion of balloon 20 may include a coating of one or more low friction materials or include one or more low friction materials in its construction. In some embodiments the assembly 10 may be used to deliver a stent 24 to a vessel bifurcation. In such embodiments a stent 24 is disposed about and crimped upon the sheath 22. The rotatability of the sheath 22 allows a stent 24 disposed thereabout to be freely rotated within a vessel or lumen to allow one or more openings of the stent to be aligned with a branch of the bifurcation.

It should be noted that the sheath can also have multiple layers. An outer layer 22a of the sheath 22 may be constructed of a softer material than that of the material used in constructing the inner layer 22b of the sheath 22. The softer outer layer will provide improved stent securement upon crimping of the stent 24. In one embodiment, a soft polymer is one with a durometer hardness of less than about 55D. Possible materials for the outer layer are a polymer like PEBAX (55D), a urethane, etc. The low friction inner layer 22b can be constructed of PTFE or HDPE.

Figure 5:
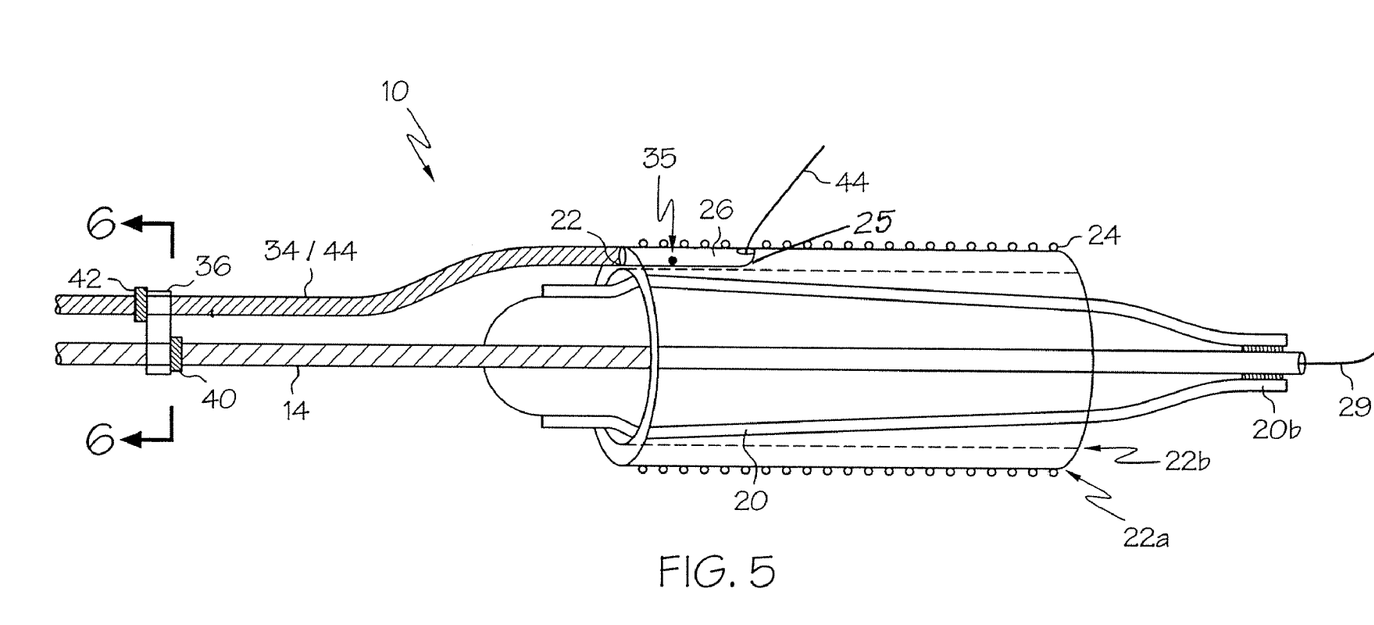
FIG. 5 is a perspective view of an embodiment of the invention wherein the assembly is shown illustrating the tether attachment and also the rotating collar and longitudinal locks.

A second shaft 25 defining the second wire lumen 26 is engaged along a portion of the sheath 22. The sheath itself can also define the second wire lumen 26. Rotational torque indicated by arrows 27 may be applied to the sheath 22 when the catheter is advanced to the bifurcation site in the following manner:

In some embodiments of the assembly 10 is advanced along two guide wires 29 and 44 as shown in FIG. 5. The first guidewire 29 is positioned in the primary passage or branch vessel and is disposed inside the inner lumen 17 of the catheter shaft 14. The second guidewire 44 diverges from the first guidewire 29 upon passage into the secondary branch in the region of the bifurcation. The inner lumen 17 of the stent delivery assembly 10 is disposed about the guidewire 29 in the primary passage while the second wire lumen 26 of the stent delivery assembly 10 is disposed about the second guidewire which extends into the secondary passage of the bifurcation. As the stent delivery assembly 10 approaches the bifurcation, the sheath 22 which is engaged to the second wire lumen 26 will then rotate so as to be aligned with the side wall passage at the bifurcation. A tether 34 can also be added in order to limit the distal movement of the sheath 22 in relation to the inner shaft 16. The tether 34 can be attached directly to the sheath at tether engagement point 11.

Figure 7:
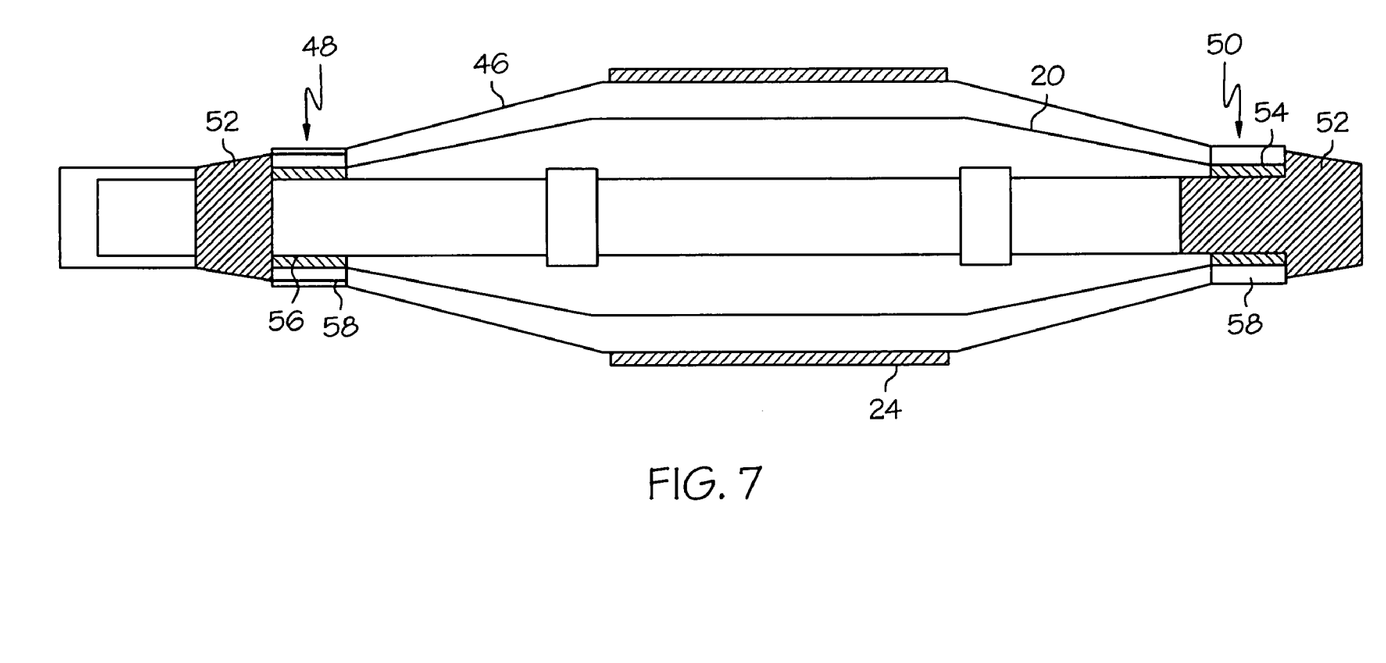
FIG. 7 is a perspective view of an embodiment of the invention wherein the assembly is shown having an outer balloon in place of the sheath.

The sheath or the outside balloon, as illustrated in FIG. 7, substantially freely rotates about the inner shaft 16 and/or balloon 20. The sheath or outside balloon may rotate less than a single degree or over 360 degrees in order to align at least one of the openings in the stent with a side branch lumen at a bifurcation site.

Figure 2A:
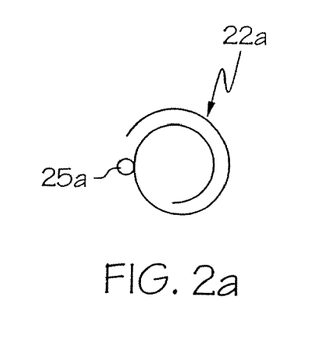
FIGS. 2a-d are cross-sectional views of sheath configurations.
Figure 2B:
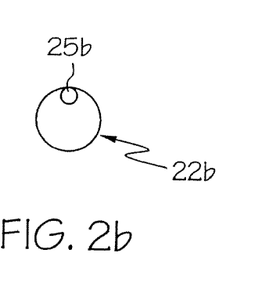
Figure 2C:
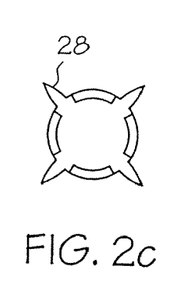
Figure 2D:
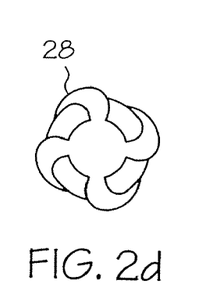

In FIGS. 2a-2c cross-sections of different embodiments of the shown sheath 22 in the unexpanded state prior to the delivery of the stent are illustrated. The second shaft 25 defining the second wire lumen 26 is engaged to the sheath 22. In another embodiment such as is shown in FIG. 2a a sheath having a second shaft 25a is attached to the sheath 22a. In a balloon expandable delivery system the sheath 22a is arranged in a coil-like structure before deployment of the stent. During delivery of the stent, the sheath 22a uncoils. In another embodiment such as is shown in FIG. 2b a sheath having a clam shell cross-section is shown in the unexpanded state. The second shaft 25b is engaged to the sheath at an end of the sheath 22b. In another embodiment such as is shown in FIG. 2c a sheath prior to delivery of the stent has a cross-section in the unexpanded state shaped in an accordion-like structure. The folds 28 in the unexpanded state can be pressed down or wrapped as shown in FIG. 2d.

Figure 3:
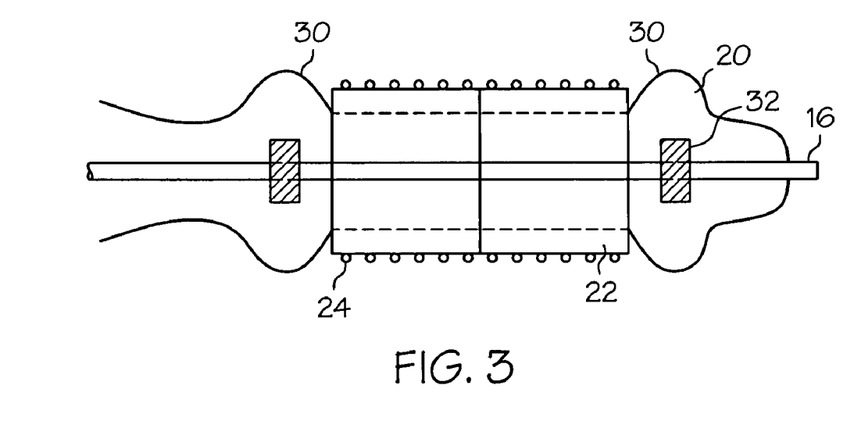
FIG. 3 is a perspective view of an embodiment of the invention wherein the assembly is shown having balloon cones on the balloon.
Figure 4:
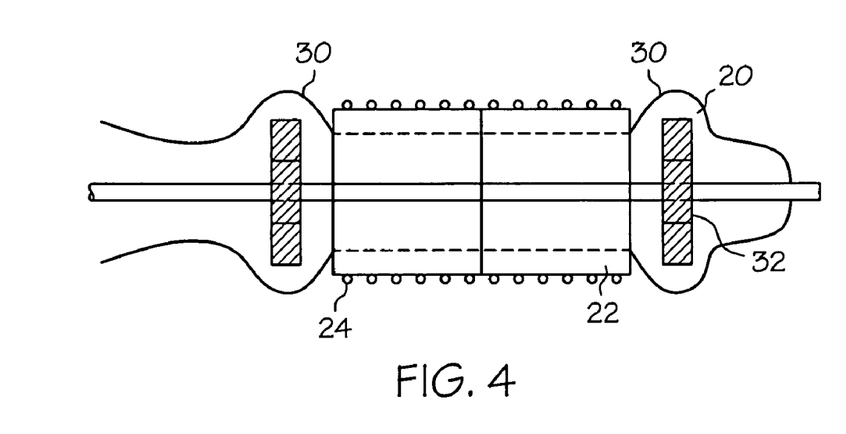
FIG. 4 is a perspective view of an embodiment of the invention wherein the assembly is shown having large diameter marking bands.

In some cases it may be desirable to provide external protection of the sheath to prevent the sheath from being longitudinally displaced during advancement of the catheter and/or delivery of the stent. In FIG. 3 an embodiment is shown wherein the balloons end portions or cones 30 are provided with a diameter about the inner catheter shaft 16 greater than the cross-sectional diameter of the sheath 22. Thus, as a result of the position of the cones 30 about the ends of the sheath 22 the longitudinal movement of the sheath 22 relative to the inner catheter shaft 16 is limited. In another embodiment shown in FIG. 4, the sheath is protected by the inclusion of one or more hubs, protrusions, marker bands 32, etc. with a diameter sufficient to prevent the sheath from moving in a longitudinal direction. These marker bands 32 act like a dam on each end of the sheath 22 by forcing portions of the balloon radially outward such that these portions of the balloon 20 have a greater diameter than the diameter of the sheath 22. In the embodiments shown in FIGS. 3 and 4 the stent 24 in either or both the expanded and the unexpanded conditions may have a greater diameter than the cones 30 while the sheath 22 does not.

In FIG. 5 an embodiment of the invention is shown wherein the assembly is provided with a safety tether 34. The tether 34 (shown in this figure overlapping the second guide wire 44) can be a simple pull wire that runs along the length of the catheter 10 and engages the sheath 22. The tether 34 can extend into the second wire lumen 26 and thereby engage the sheath 22 or the second shaft 25 at an engagement point 35. The safety tether 34 can also attach to the sheath 22 directly as shown in FIG. 1 at tether engagement point 11.

Figure 6:
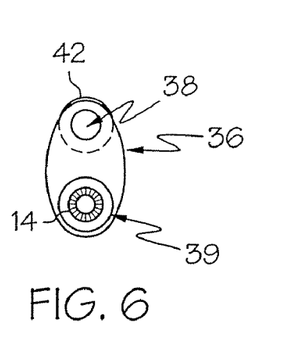
FIG. 6 is a cross-sectional view of the rotating collar from view A-A of FIG. 5.

As shown in the cut away portion of FIG. 5 and in FIG. 6 the catheter 10 may include a rotating collar 36 having a second guide wire collar lumen 38 and an outer catheter shaft collar lumen 39 which is disposed about the outer catheter shaft 14. A distal longitudinal lock 40 disposed about the catheter shaft and both adjacent and distal to the collar 36 limits longitudinal movement of the collar 36. The distal longitudinal lock 40 has a diameter greater than the diameter of the outer catheter shaft collar lumen 39. The proximal longitudinal lock 42 disposed about a second guide wire 44 has a greater diameter than the second guide wire collar lumen 38, thus limiting the wire 44 from distal movement beyond the point when the proximal longitudinal lock 42 comes into contact with the second guide wire collar lumen 36.

In FIG. 7 an outer balloon 46 which rotates around the inner balloon 20 is used in place of a sheath 22. In such embodiments the outer balloon 46 is sealed at first end 48 and second end 50 of the catheter 10. Balloon movement stoppers 52 limit longitudinal movement of the balloons. The outer balloon 46 can be constructed of a low friction material such as PTFE or HDPE which allows the outer balloon 46 to freely rotate about the inner balloon 20. The stent 24 is disposed about and crimped upon the outer balloon 46. It should be noted that the outer balloon can also have multiple layers. An outer layer of the outer balloon 46 may be constructed of a softer material than that of the material used in constructing the inner layer of the outer balloon 46. Where the balloon is provided with a softer outer layer, the softer outer layer may provide improved stent securement upon crimping of the stent 24. In one embodiment, a soft polymer is one with a durometer hardness of less than about 55D. Possible materials for the outer layer are a polymer like PEBAX (55D), a urethane, etc. The low friction inner layer of the outer balloon 46 can be constructed of PTFE or HDPE and/or other suitable materials.

In the embodiment shown in FIG. 7 the outer balloon 46 is rotatable about the inner balloon 20. Gap 58 (shown on only one end, first end 48) acts as a friction reducing mechanism between outer balloon seal site 54 and inner balloon seal site 56. Gap 58 includes a friction reducing fluid, a low friction material, a bearing system, etc., or any combination thereof.

Figure 8:
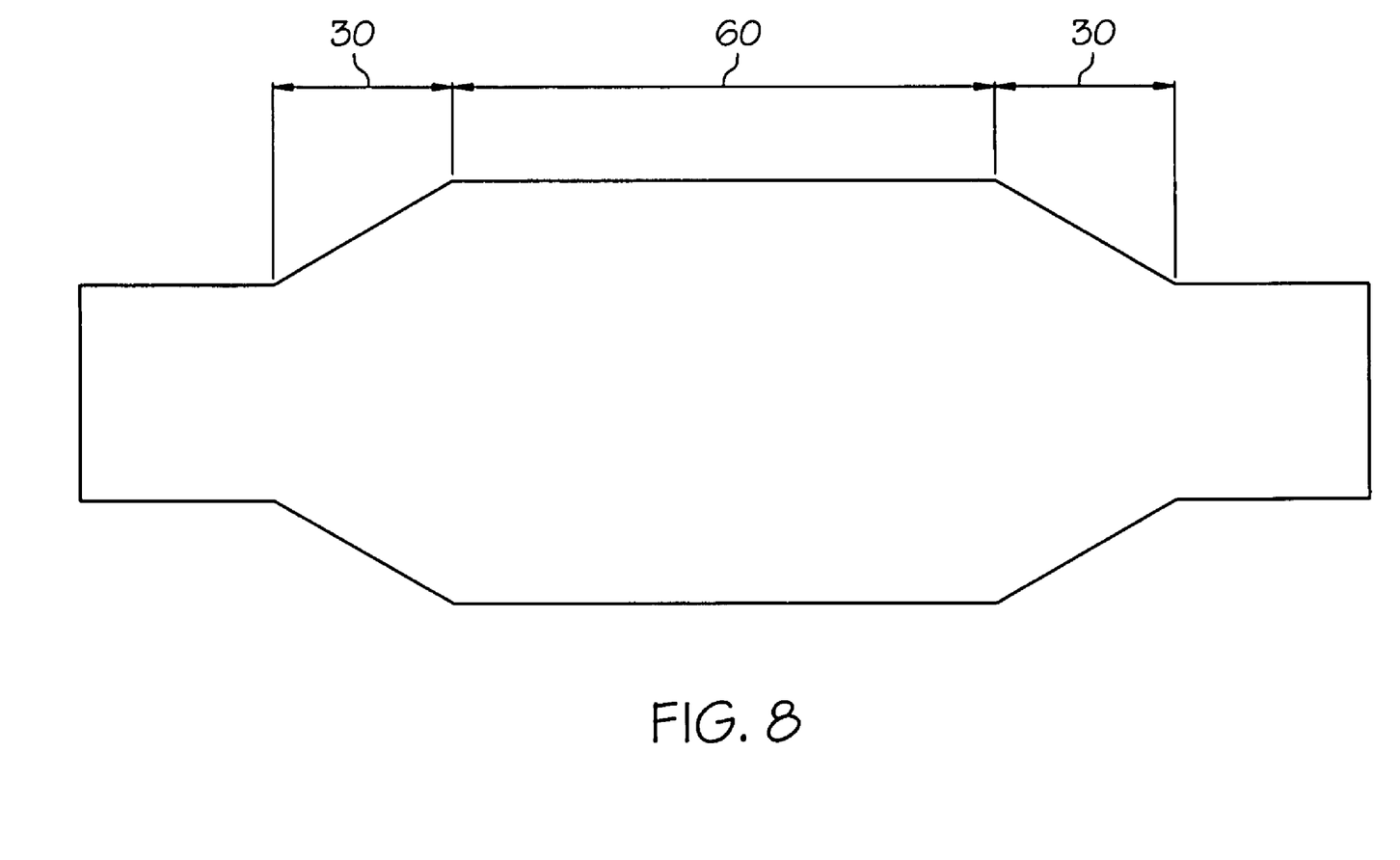
FIG. 8 is a perspective view of a catheter balloon illustrating the body portion and the cone portions of the catheter balloon.

In the embodiment shown in FIG. 8 the cones 30 and body portion 60 of the catheter balloon 20 are shown. In some embodiments of the invention the sheath 22 is of the substantially same length as the body portion 60 of the catheter balloon 20. In some embodiments the sheath 22 is disposed substantially on the body portion 60 of the balloon 20. In other embodiments the sheath 22 extends longitudinally such that a portion of the sheath 22 is disposed about at least one of the cone portions 30.

Figure 9:
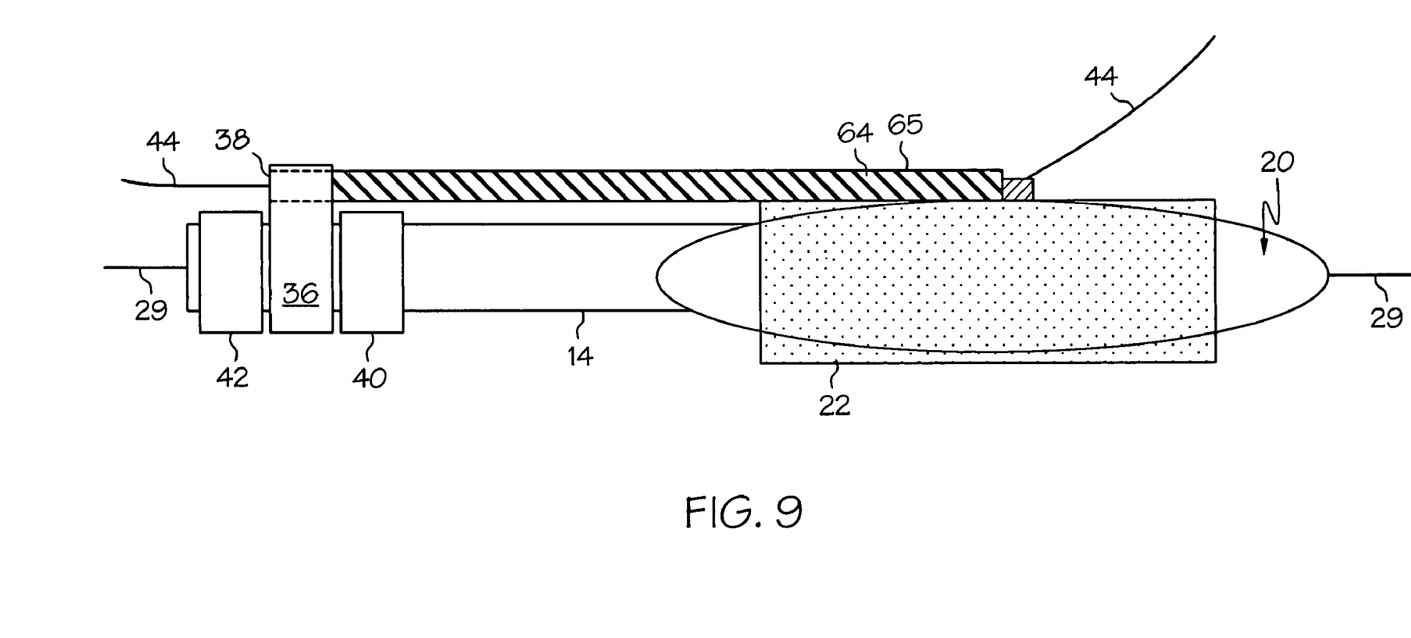
FIG. 9 is a perspective view of an embodiment of the invention wherein the assembly is shown having a hypotube which is disposed in the second guide wire collar lumen.
Figure 10:
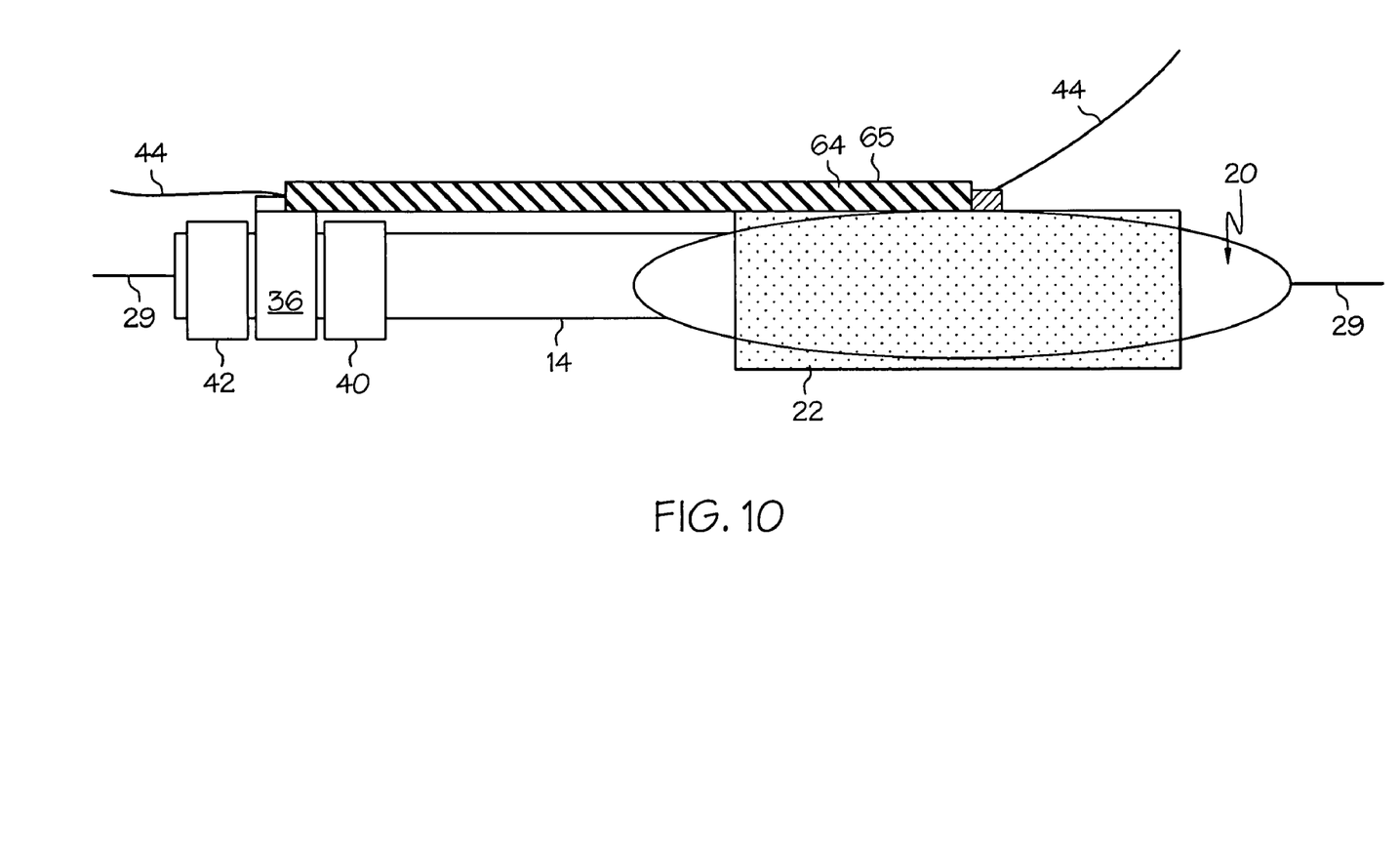
FIG. 10 is a perspective view of an embodiment of the invention wherein the assembly is shown having a hypotube engaged to the collar.

In the embodiments of FIGS. 9 and 10 a hypotube 64 is engaged to the collar 38 and the sheath 22. The hypotube 64 may comprise stainless steel or it may comprise a polymer. The hypotube 64 may be constructed to be spiral cut. The spiral cut 65 may include scoring, cutting, indenting, perforating, puncturing, etc. The hypotube 64 may thus be firm in the longitudinal direction but may also be flexible due to the spiral cut.

FIGS. 9 and 10 also illustrate embodiments having both the proximal longitudinal lock 42 and the distal longitudinal lock 40 disposed about the outer catheter shaft 14 rather than as shown in FIGS. 5 and 6 wherein one longitudinal lock is disposed about the guidewire 44 or safety tether 32.

FIG. 9 specifically illustrates an embodiment wherein the hypotube 64 is disposed in the second guide wire collar lumen 38. The hypotube 64 may be disposed in only a portion of the second guide wire collar lumen 38. The collar 36 rotates along with the sheath 22 and thus may rotate simultaneously and/or with equal degrees of rotation. In FIG. 10 the hypotube 64 is engaged to an outside surface of the collar 36. In both FIGS. 9 and 10 engagement of the hypotube 64 to the collar 36 and sheath 22 can be through chemical welding, heat welding, laser welding, chemical bonding, adhesives, fastening devices, etc.

The invention has been described with reference to the embodiments. Obviously, modifications and alterations will occur to others upon a reading and understanding of this specification. For example, the illustrated embodiments use a balloon to expand the stent although, as briefly noted above, a self expanding or self deploying stent can be used without departing from the features of the present invention. Likewise, using a fixed wire on the distal end of the apparatus is also recognized as being consistent with the features of the present invention. Moreover, the embodiments describe a side branch hypotube, either split or unsplit, that is associated with the side branch guide wire. It will be further appreciated that the side branch guide wire could be carried and/or released in a variety of other ways. The invention is intended to include all such modifications and alterations thereof.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A medical device comprising:
   a balloon catheter shaft having a catheter balloon, the catheter balloon having a length, a sheath disposed about the catheter balloon, the sheath being substantially freely rotatable about the catheter balloon, no portion of the sheath being more than about 5 centimeters proximal to a most proximal portion of the balloon;
   a stent having a side opening defined in a sidewall of the stent between proximal and distal ends of the stent, the stent extending around at least a portion of the sheath; and
   a guidewire extending through a portion of the sheath and the stent side opening.

2. The medical device of claim 1, wherein the balloon catheter shaft defines a first guide wire lumen, and the sheath at least partially defines a second guide wire lumen.

3. The medical device of claim 2, wherein the guidewire extends through the second guidewire lumen.

4. The medical device of claim 3, wherein the stent is constructed and arranged for use in a bifurcation.

5. The medical device of claim 3, wherein the stent is at least partially self-expanding.

6. The medical device of claim 3, wherein the stent is at least partially constructed of a shape memory material.

7. The medical device of claim 2, wherein a rotating collar is positioned about the second wire lumen and the balloon catheter shaft.

8. The medical device of claim 7, wherein a first longitudinal lock is positioned about the second wire lumen and proximal to the rotating collar, and a second longitudinal lock is positioned about the balloon catheter shaft and distal to the rotating collar such that the longitudinal position of the sheath and collar is maintained.

9. The medical device of claim 1, wherein the sheath is at least partially constructed of a shape memory material.

10. The medical device of claim 1, wherein the sheath is constructed of at least one homogeneous layer.

11. The medical device of claim 10, wherein the sheath comprises an inner surface, at least a portion of the inner surface having a lower frictional interface than an adjacent portion.

12. The medical device of claim 10, wherein the sheath is constructed with a soft durometer polymer.

13. The medical device of claim 10, wherein the sheath is constructed of a polymer with a durometer hardness of less than about 55D.

14. The medical device of claim 1, wherein the sheath is at least partially constructed of multiple layers.

15. The medical device of claim 14, wherein at least one of the layers is constructed of a first material having different properties from a second material found in at least one other layer.

16. The medical device of claim 14, wherein an inner layer of the sheath is in contact with the balloon, the inner layer constructed of at least one low friction material.

17. The medical device of claim 16, the low friction material is selected from the group consisting of PTFE, HDPE, or any combination thereof.

18. The medical device of claim 14, wherein there is an outer layer of a soft durometer polymer suitable for securing a stent to the sheath.

19. The medical device of claim 1, wherein the sheath has an expanded state when the balloon is in an expanded condition and an unexpanded state when the balloon is in an unexpanded condition.

20. The medical device of claim 19, wherein the sheath rotates substantially freely about the balloon when the sheath is in both the unexpanded state and the expanded state.

21. The medical device of claim 1, further comprising at least one safety tether.

22. The medical device of claim 21, wherein the at least one safety tether is a pullwire, the pullwire being positioned external of at least one of the guide wire lumens.

23. The medical device of claim 21, wherein the at least one safety tether is a pullwire, the pullwire being disposed in at least one of the guide wire lumens.

24. The medical device of claim 1 wherein the length of the sheath is no greater than 2 centimeters longer than the length of the balloon.

25. A catheter assembly, comprising:
a main catheter shaft;
a balloon positioned at a distal end of the main catheter shaft;
a sheath extending around at least a portion of the balloon, the sheath being rotatable relative to the balloon; and
a tether member coupled to the sheath for axial positioning of the sheath relative to the balloon, the tether member extending proximally from the sheath.

26. The catheter assembly of claim 25, wherein the tether is a pullwire.

27. The catheter assembly of claim 25, further comprising a stent extending around at least a portion of the sheath, the stent including at least one side opening defined in a sidewall of the stent between proximal and distal ends of the stent.

28. The catheter assembly of claim 27, further comprising a first guidewire lumen extending through the balloon, and a second guidewire lumen extending between the balloon and the stent.

29. The catheter assembly of claim 28 further comprising a first guidewire that extends through the first guidewire lumen, and a second guidewire that extends through the second guidewire lumen and the at least one side opening of the stent.

30. The catheter assembly of claim 27, wherein the tether member is positioned within at least one of the first and second guidewire lumens.

31. The catheter assembly of claim 25, wherein the tether member is connected directly to the sheath.

* * * * *